United States Patent
Mevel et al.

(12) 
(10) Patent No.: US 10,864,369 B2
(45) Date of Patent: Dec. 15, 2020

(54) IMPLANTABLE PROBE COMPRISING A PERFORATED SLEEVE

(71) Applicant: SORIN CRM SAS, Clamart (FR)

(72) Inventors: Hervé Mevel, Chastre (BE); Stéphane Befahy, Brussels (BE); Vincent Callegari, Corbais (BE)

(73) Assignee: Sorin CRM SAS, Clamart (FR)

( * ) Notice: Subject to any disclaimer, the term of this patent is extended or adjusted under 35 U.S.C. 154(b) by 14 days.

(21) Appl. No.: 15/769,236

(22) PCT Filed: Oct. 18, 2016

(86) PCT No.: PCT/EP2016/074996
§ 371 (c)(1),
(2) Date: Apr. 18, 2018

(87) PCT Pub. No.: WO2017/067939
PCT Pub. Date: Apr. 27, 2017

(65) Prior Publication Data
US 2018/0304071 A1 Oct. 25, 2018

(30) Foreign Application Priority Data
Oct. 19, 2015 (FR) .................................... 15 59951

(51) Int. Cl.
*A61N 1/05* (2006.01)
*A61N 1/36* (2006.01)

(52) U.S. Cl.
CPC ....... *A61N 1/0556* (2013.01); *A61N 1/36053* (2013.01); *A61N 1/36114* (2013.01)

(58) Field of Classification Search
CPC .............. A61N 1/0556; A61N 1/36053; A61N 1/36114
See application file for complete search history.

(56) References Cited

U.S. PATENT DOCUMENTS

| | | | |
|---|---|---|---|
| 4,602,624 A | 7/1986 | Naples et al. | |
| 4,940,065 A | 7/1990 | Tanagho et al. | |
| 5,251,634 A | 10/1993 | Weinberg | |

(Continued)

OTHER PUBLICATIONS

Search Report on European Application No. 16194476 dated Dec. 22, 2016. 1 page.

(Continued)

*Primary Examiner* — Catherine M Voorhees
(74) *Attorney, Agent, or Firm* — Foley & Lardner LLP

(57) ABSTRACT

The disclosure relates to implantable probes. An implantable probe includes a sleeve capable of being wound around an elongate organ of cylindrical shape, and includes a sheet of elastically deformable material that supports at least one electrode. The sheet is prestressed in such a way as to allow it to self-wind from an initial position, in which the sheet is kept stressed in the deployed state, to a final position, in which the sheet is wound freely in a spiral to form a sleeve around the organ, with the first face, which supports the electrodes, being directed towards the inside. The sheet is delimited by an outer lateral edge of the sleeve after winding, an inner lateral edge of the sleeve after winding, and a first transverse edge and a second, opposite transverse edge. The sheet includes perforations located in proximity to the first and/or second transverse edge.

20 Claims, 3 Drawing Sheets

(56) References Cited

U.S. PATENT DOCUMENTS

| | | | |
|---|---|---|---|
| 9,956,398 B2* | 5/2018 | Callegari | A61N 1/0556 |
| 2009/0210042 A1* | 8/2009 | Kowalczewski | A61B 5/04001 |
| | | | 607/118 |
| 2013/0165996 A1* | 6/2013 | Meadows | A61N 1/0556 |
| | | | 607/60 |
| 2013/0231726 A1 | 9/2013 | Johnson et al. | |
| 2016/0263376 A1* | 9/2016 | Yoo | A61N 1/36007 |

OTHER PUBLICATIONS

International Search Report and Written Opinion on International Application No. PCT/EP2016/074996 dated Apr. 27, 2017. 9 pages.

* cited by examiner

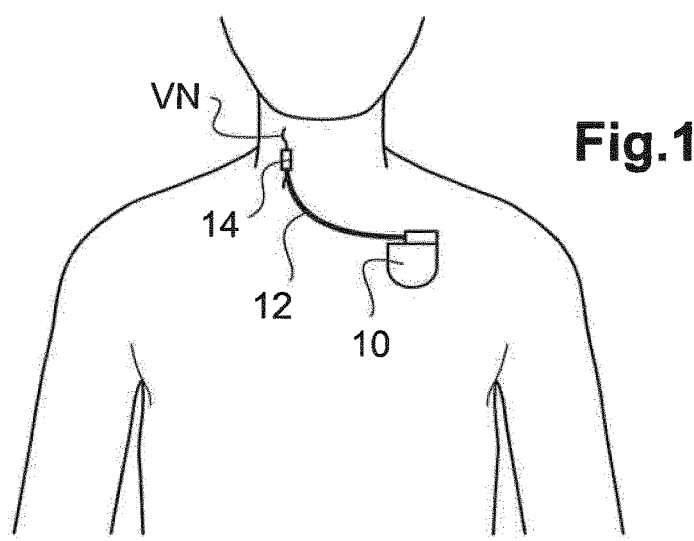
Fig.1
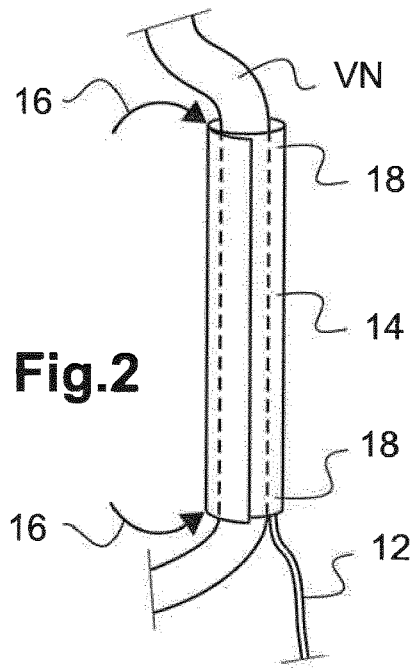
Fig.2
Fig.3
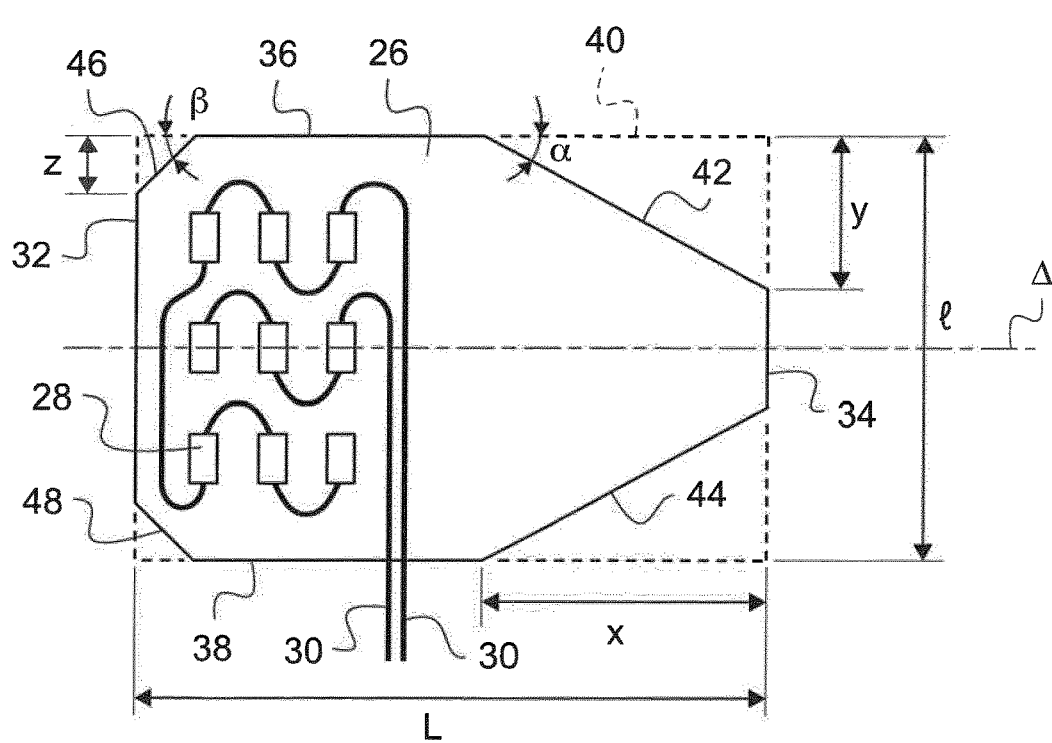

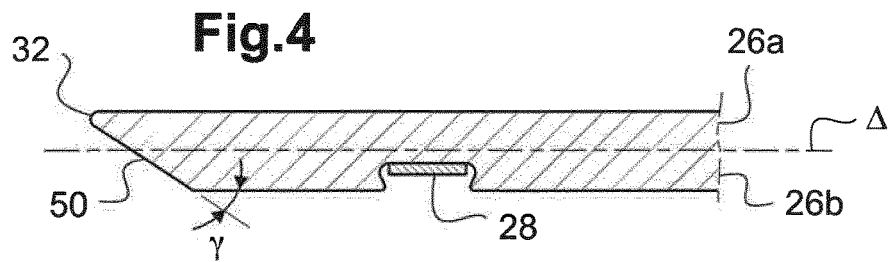
Fig.4
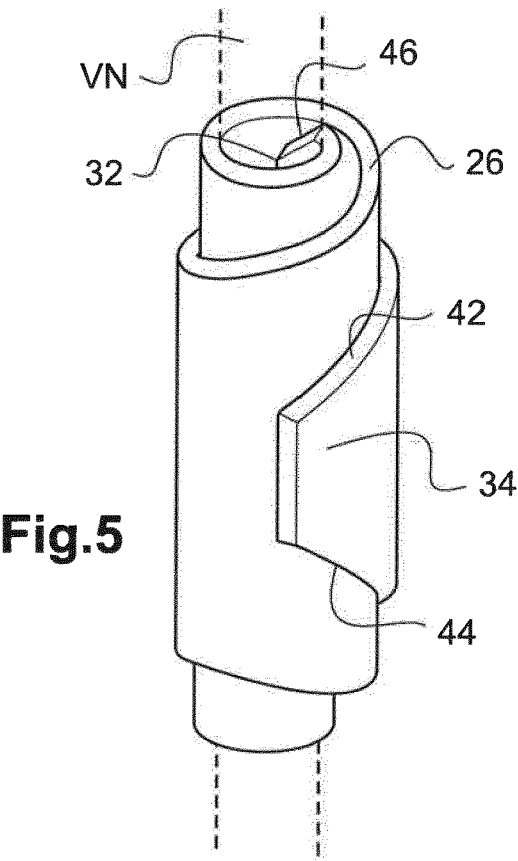
Fig.5
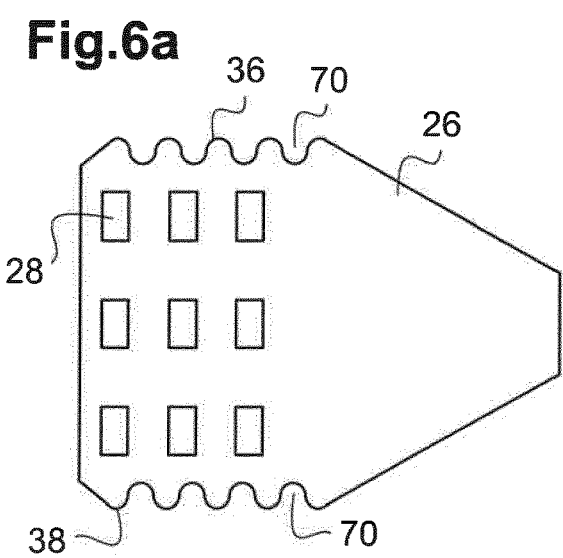
Fig.6a
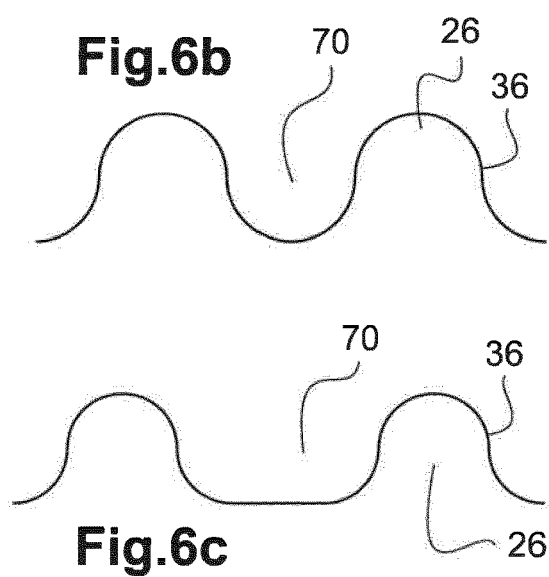
Fig.6b
Fig.6c

IMPLANTABLE PROBE COMPRISING A PERFORATED SLEEVE

CROSS-REFERENCE TO RELATED PATENT APPLICATIONS

This application is a 371 U.S. National application of International Application No. PCT/EP2016/074996, filed Oct. 18, 2016, which claims the benefit of and priority to French Patent Application No. 1559951, filed Oct. 19, 2015, which is incorporated herein by reference in its entirety.

BACKGROUND

The invention relates to "active implantable medical devices" as defined by Directive 90/385/EEC of 20 Jun. 1990 of the Council of the European Communities, and more specifically to devices capable of stimulating an elongate organ of cylindrical shape and/or picking up electrical potentials from such an organ.

The invention more particularly relates to the stimulation of the nerves, especially the stimulation of the vagus nerve in the case of therapies referred to as VNS (Vagus Nerve Stimulation).

However, such application has no restrictive character, as the invention may be used to stimulate/detect any other organ, or for other purposes such as the local delivery of an active agent, etc. to this organ, providing that the target organ has an elongate cylindrical shape.

Nervous system stimulation is a recognized therapy in respect of many disorders such as epilepsy, pain, heart failure, apnea, obesity, etc.

The devices used for this purpose include a probe featuring an electrode implanted on the vagus nerve and a generator delivering electrical pulses to said electrode.

VNS therapy consists in generating bursts of repetitive pulses, synchronized or not to the heart rate depending on the disorder that is to be treated, these pulses being superimposed on the signals naturally conveyed by the nervous system, arranged in a closed loop. Vagus nerve stimulation may act efferently, directly towards an organ, or afferently, to the brain so as to influence the central nervous system: the arbitrary signal comprised of VNS pulses will then be interpreted by the central nervous system as a solicitation, that it will attempt to compensate by counteracting it, thus preventing the expected effects to be produced.

The invention relates more specifically to the device being implanted at the electrode/nerve interface, which keeps the electrodes in direct contact with the nerve or very close to it. Given the elongate and approximately cylindrical configuration of a peripheral nerve such as the vagus nerve, the most commonly used device is in the form of a tubular sleeve, wrapped around the nerve. The sleeve is generally made of an elastomer such as silicone, due to the excellent biocompatibility of this material, and supports on its inner face, applied against the nerve, the stimulation (and/or detection) electrodes.

Such a sleeve is for example disclosed in U.S. Pat. No. 4,602,624 A. The sleeve disclosed therein is made up of two sheets of elastomer laminated together, one of them having been previously stretched in a preferred prestressing direction. The resulting composite sheet is then cut to obtain a rectangular piece which, due to the prestressing of one of the sheets, will naturally tend, in a free state, to wind in a spiral around an axis perpendicular to the prestressing direction (a "spiral" is a plane curve being regularly wound around a point from which it deviates more and more).

Compared with a rigid sleeve, the sleeve described herein has the advantage of being simple to implement: all the surgeon has to do is to unroll it, place it under the nerve and release it, for the sleeve to come and wrap itself around the nerve. In addition, the sleeve is self-adaptable: in fact, immediately after implantation, a normal inflammatory process results in a temporary swelling of the nerve, which then disappears. By choosing a flexible spiral sleeve with an inner diameter at rest slightly smaller than the diameter of the nerve, the sleeve—with its electrodes—will always remain tightly pressed against the nerve even if the diameter thereof varies, and thus with no risk of excessive pressure that might cause irreversible damage to nervous tissues.

However, this device is not without drawbacks.

A first drawback appears at the time of implantation: to install the sleeve after reaching the target nerve, the surgeon has to pull the nerve out of the incision he has made, so as to slide the unrolled sleeve into place at the chosen location. When so doing, the traction exerted on the nerve can result locally, towards the ends of the sleeve, in relatively high loads on the nervous tissue, which might possibly damage it. Another possible cause of damage to the nerve is the processing time, which may expose the nerve to air for too long. It is therefore necessary to perform the sleeve implantation process in a very short time, with limited handling of the nerve, as far as possible. Also, during implantation, the corners of the sleeve may tend to wind by themselves thereby interfering with the implantation, which complicates the task of the surgeon.

A second drawback, which appears after implantation, is that the innermost edge of the sleeve, that is to say the edge wound around the nerve, bears against the nerve thereby exerting a pressure along the contact line that tends to constrain or even distort the nerve, with potentially deleterious effects. The stiffness of the sleeves can also induce unacceptable shearing forces at sleeve ends. An additional risk, at the time of implantation, is that the surgeon may have let the outer edge portion of the sleeve wind in the opposite direction, then forming a second coil in the opposite direction of the first. The radius of curvature is thus altered, which may cause an increase in the thickness of the sleeve.

A third drawback has to do with the manufacturing process. As mentioned above, the sleeve is produced by laminating together two elastomeric sheets, with a directional prestressing applied to one of them. As these sheets are very thin (their typical thickness is approximately 100 µm), problems of homogeneity in the material and of thickness tolerance may appear on the extent of the surface of a single sheet as well as between two sheets, thus limiting the reproducibility of the production process for sleeves. It is actually possible to overcome this disadvantage by using large sheets, but with a negative impact on the industrial process. It is also possible to use thicker sheets, that are easier to control throughout the process, but with an increased risk of damaging the nerve due to lower flexibility and hence a lesser ability of the sleeve to conform to the morphology of the nerve in the implantation zone. Lastly, a fourth drawback is due to the use of an insulating material as support for the electrodes and the blunt ending of sleeve ends, the result of which is the creation of virtual anode or cathode-type electrodes, resulting in blocking effects or unwanted stimulations.

It is also known to the document U.S. Pat. No. 5,251,634, a sleeve for an implantable probe composed of a plurality of spiral loops is disclosed. A pair of electrically conductive filament bands is incorporated into the material of two spiral loops respectively. Other helixes forming the sleeve are used to secure the sleeve onto the nerve.

This technical solution also has several drawbacks. In particular, implanting such a device with a plurality of spiral loops around the nerve is hard to implement. Additionally, stimulation currents to be applied to the nerve are not applied solely on the nerve itself since no continuous protection of the sleeve is provided. Finally, a spiral loop sleeve is not adapted to receiving electrodes meant to feature several contact points, in particular for tripolar stimulation.

Other sleeves for an implantable probe have also been designed, in particular of cylindrical shape with a longitudinal opening allowing the implantation of the sleeve around the nerve. Various sleeve locking systems were then designed. However, these sleeves have a fixed diameter and in order not to damage the nerve when implanting the sleeve, the chosen sleeve should be larger than the diameter of the nerve. Hence a proper connection between the sleeve and the nerve is not possible and therefore the electrodes are not kept in contact with the nerve.

The need therefore remains for a self-winding sleeve made of thin elastomer that can be produced according to an effective industrial process, with a high degree of reproducibility while suppressing the known side effects of existing sleeves.

SUMMARY

The purpose of the invention is to solve these problems by proposing a new self-winding spiral sleeve structure:
that facilitates quick implantation by the surgeon, without applying excessive stress loads on the nerve, and in particular that can preclude the risk of generating a shearing force on the edges of the sleeve;
that respects the anatomic integrity of the nerve after implantation while still providing a satisfactory hold of the sleeve at the implantation location selected;
which can be produced by an optimized process in respect of industrial constraints and
that eliminates the need for generating virtual electrodes.

To this end, the invention provides an implantable probe comprising a self-winding sleeve such as described in particular by the aforementioned U.S. Pat. No. 4,602,624 A document, that is to say comprising, in a manner already known in itself, a sleeve capable of being wound around an elongate organ of cylindrical shape such as a nerve, and comprising a sheet of elastically deformable material that supports at least one electrode for stimulation/detection purposes on a first face of the sheet. The sheet is prestressed in such a way as to allow it to self-wind from an initial position, in which the sheet is kept stressed in the deployed state, to a final position, in which the sheet is wound freely in a spiral to form a sleeve around the organ, with the first face, which supports the electrodes, being directed towards the inside. The sheet is delimited by an outer lateral edge of the sleeve after winding, an inner lateral edge of the sleeve after winding, and a first transverse edge joining first homologous ends of the first lateral edge and of the second lateral edge, and a second opposite transverse edge joining second homologous ends of the first lateral edge and of the second lateral edge.

In a way typical of the invention, the sheet comprises a plurality of perforations located in proximity to the first or second transverse edge.

According to various subsidiary characteristics:
the perforations are triangular in shape.
the triangles have rounded corners.
the perforations are substantially round in shape.
the perforations are located in at least one zone extending up to 25% of the width of the sheet in proximity to the first and/or second transverse edge, the width of the sheet being defined by the distance between the first and the second transverse edge.
the perforations are formed on the first and/or second transverse edge and said edge is saw-tooth shaped.
the outer lateral edge is, at both ends, connected to the two transverse edges via a respective bevel edge forming an oblique angle with respect to the direction of the largest dimension of the sheet.
the bevel edge extends over 15 to 60% of the extent of the sheet in the direction of its largest dimension.
the perforations are located in proximity to the first and/or the second non-beveled transverse edge.

BRIEF DESCRIPTION OF THE DRAWINGS

An exemplary embodiment of the present invention will now be described, with reference to the appended drawings, in which identical or functionally similar items are referenced under the same item numbers throughout the figures.

FIG. 1 is a general view illustrating a VNS stimulation assembly, showing the generator and the vagus nerve, as well as the probe that is used.

FIG. 2 is a view of a sleeve according to the prior art, wound around the vagus nerve during the implantation process.

FIG. 3 is a plan view of the sleeve in the unrolled configuration such as the sleeve is in, at the time of manufacture.

FIG. 4 is a section in the thickness direction of the sleeve of FIG. 3, showing a partial view in the region of one of the edges, and in particular the superimposed, two-layered structure laminated together.

FIG. 5 is a perspective view of the sleeve of FIG. 3 in its free configuration, wound around itself.

FIG. 6a is a plan view of one embodiment of the sleeve according to the invention, in the unrolled configuration, and FIGS. 6b and 6c are partial views of a longitudinal edge of the sleeve.

DETAILED DESCRIPTION

Figure 7A:
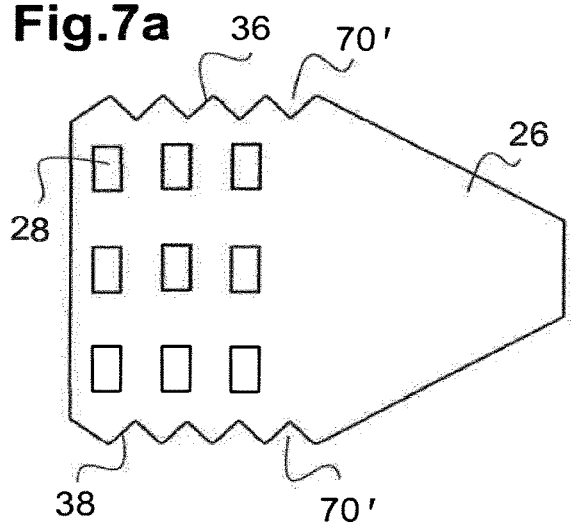
FIG. 7a is a plan view of a second embodiment of the sleeve according to the invention, in the unrolled configuration.

An exemplary embodiment of the present invention will now be described, in the form of a probe for vagus nerve stimulation, this example being in no way restrictive, as mentioned in the introduction.

In FIG. 1, item 10 refers to the housing of an implantable VNS stimulation generator. The generated stimulation pulses are delivered by a probe 12 bearing at its distal portion a sleeve 14 provided with electrodes applied against the vagus nerve VN and apt to stimulate such nerve by the bursts of pulses produced by the generator 10.

FIG. 2 is a view of a sleeve 14 according to the prior art, wound around the vagus nerve VN during the implantation procedure.

To install the sleeve, the surgeon had to pull the vagus nerve VN out of the incision he had made, so as to slide the unrolled sleeve into place at the chosen location. After winding itself in a spiral, the sleeve 14 looks as shown in FIG. 2. In this particular configuration, stresses are exerted by the cylindrical sleeve in region 18 due to the discontinuity in rigidity between the part of the nerve enclosed within the sleeve 14, and the free portion situated beyond the sleeve. This discontinuity between a portion where the nerve is locked in place and one in which it is free, locally creates stresses at the point of transition, which stresses may damage the nervous tissues.

Another drawback, that is also specific to sleeves according to the prior art, is that if one considers the innermost end of the sleeve 14 that is spirally wound, as this end happens to be enclosed within the remaining part of the sleeve, stresses are accordingly exerted on the nerve VN in region 18, located in the vicinity of this end (stresses schematically shown by arrows 16) which have the effect of deforming the nerve permanently, with potentially deleterious effects.

Another drawback is linked to the creation of virtual electrodes as explained below.

Neural stimulation is an artificial activation of the nerve fiber, this activation being a mild electrical stimulation, in particular by applying a short pulse of electric current on the membrane of the nerve fiber that is called action potential.

However, the inside of the nerve membrane is not accessible and the current through the membrane has to be obtained by applying an external potential field.

The laws of Ohm and Kirchhov indicate that the current penetrating the membrane (Im) is defined as follows:

$$Im \approx d(\sigma z \cdot d(Uz))/dz^2,$$

Wherein z is the nerve diameter, $\sigma z$ is the electrical conductivity along the axis of the nerve, and $Uz$ is the potential applied to the membrane.

The outer membrane flow activates the membrane by depolarization while the inner membrane flow inhibits the activation or the propagation of action potentials by hyperpolarization.

The electrode support material, in general silicone elastomer, has very low conductivity as compared to the biological fluids and tissues surrounding the sleeve.

Thus, the current generated by the electrodes along the nerve will encounter a sudden change in the conductivity of the material ($\sigma z$) at both ends of the sleeve. This results in the generation of internal currents corresponding to an anode-type virtual electrode, or external currents corresponding to a cathode-type virtual electrode, through the membrane. These virtual electrodes can stimulate the nerve, or otherwise block the transmission of an action potential. These effects are a nuisance in most cases because they cannot be controlled.

Another drawback of this device according to prior art is due to the fact that virtual anodes and virtual cathodes do not act only on the nerve, but also on the environment of the sleeve wrapped around the nerve, namely the muscles, skin or other nerves, occasioning side effects in the patient.

Finally, as such a sleeve exhibits some rigidity, in particular on the edges of the sleeve, it may damage the nerve by introducing a pressure on the nerve that will tend to constrain and distort the nerve. In addition, the edges of the sleeve can exert shearing forces on the nerve. These various drawbacks, as well as those described in the introduction, can be solved by a sleeve constructed according to the teachings of the invention, shown in FIGS. 3 to 9, and more specifically FIGS. 6 to 9.

FIG. 3 is a plan view of the sleeve in the unrolled configuration such as the sleeve is in, at the time of manufacture.

The sleeve 26 according to the invention is made from two sheets of elastomer 26a and 26b (FIG. 4) laminated together, for example of silicone, one of the sheets having been subjected beforehand to a stretching prestressing in direction Δ, which in this example is the direction of the largest dimension of the sheet 26. As explained in the aforementioned U.S. Pat. No. 4,602,624 A, this technique is used to make the sleeve spirally self-winding when sheet 26, after manufacturing of the sleeve, is no longer subjected to any external force, resulting in the wound configuration shown in FIG. 5. In this way, the sheet 26 is prestressed in such a way as to allow it to self-wind from an initial position, in which the sheet is kept stressed in the deployed state, to a final position, in which the sheet is wound freely in a spiral to form a sleeve around the organ, with the first face, which supports the electrodes, being directed towards the inside.

Silicone is preferably chosen as the base material for the implantable sleeve, due to its excellent biocompatibility properties, both in terms of bio-tolerance (the implant does not induce damage to host: absence of toxicity and mechanical damage to tissues) and biostability (the implant can withstand the conditions induced by the host).

The sheet 26 supports, in the region intended to come into contact with the vagus nerve after it is wound (the region situated to the left in FIG. 3), a certain number of electrodes 28 subsequently applied onto the surface of the sheet or embedded in the thickness of the elastomeric material. These electrodes 28 are connected to wires 30 meant to be connected to the pulse generator 10. In the example illustrated in FIG. 3, these electrodes 28 are uniformly distributed along the winding axis of the sleeve 26 and they are interconnected so as to constitute a matrix of contacts of quasi-tripolar type (anode/cathode/anode or vice versa) connected to the corresponding micro-cables 30.

The sleeve is made from the sheet 26 which has a rectangular shape, with an inner first lateral edge 32 forming a first width (that comes within the spiral once the sleeve is wound), a second outer lateral edge 34 on the opposite side forming a second width (that comes to be on the outer side of the sleeve when it is wound), and a first transverse edge 36 joining first homologous ends of the first lateral edge 32 and the second lateral edge 34, and a second transverse edge 38 on the opposite side joining second homologous ends of the first lateral edge 32 and the second lateral edge 34.

The right-angled corners of the rectangular sheet are cut (by stamping, by cutting with a blade or any other suitable manufacturing process) so as to eliminate the regions delimited by the dashed line 40, thereby forming bevel edges 42, 44, 46, 48. In the region situated on second lateral edge 34, the bevel edges 42 and 44 form with the lengths 36, 38 (which are themselves parallel to the axis A) an angle a of 20° to 45°, for example, so that the extent of portion 40 that has been removed to form the bevel extends over a length x in the order of 15 to 60% of the total length L of the sheet 26, and over a width y in the order of 20 to 50% of the total width of the sheet 26. As for the bevels 46, 48 on the opposite side, they form an angle ft of 30° to 60° and extend over a width z of 10 to 25% of the total width of the sheet 26.

Moreover, in the thickness direction, the first lateral edge 32 forms a chamfered edge 50, the chamfer being turned towards the face of the sheet that is to be applied against the nerve (that is to say the face supporting the electrodes 28). This chamfer is inclined at an angle y between 20° and 45° for example.

With the configuration described above, in its wound configuration the sleeve according to the invention takes the form illustrated in FIG. 5, with an appearance resembling a crescent-shaped pastry (in a straight shape), because of bevel edges 42, 44 which give the wound portion on the outer side a tongue-shaped aspect.

This tongue facilitates implantation operations, insofar as the sleeve can be handled without the risk of collapsing the corners of the sleeve inwardly, which would result in increased thickness with detrimental effects.

In addition, this "crescent-shaped" aspect makes it immediately visible, should a winding be inadvertently inverted, so that the region supporting the electrodes (to the left in FIG. 3) would end up covering the opposite region (the area located to the right in FIG. 3), whereas it should be the opposite. As bevels 46, 48 are much smaller in size than bevels 42, 44, the typical tongue-shaped aspect as shown in FIG. 5 would be missing, thereby immediately revealing the inverted winding direction.

Another advantage of this crescent shape lies in the stiffness gradient of the sleeve in its wound configuration, with the rigidity gradually decreasing from the center to the ends of the sleeve. The increased flexibility at the ends makes it possible to exert less stress locally on the nerve (in contrast to prior art sleeves, as shown in FIG. 2), while in the central region the clamping force exerted by the sleeve is maximum, thus holding the electrodes firmly pressed against the nerve.

To produce the sleeve, relatively thin sheets (approximately 100 μm thick) can be used, resulting in very flexible sleeves, which are very well tolerated, without compromising on ease of installation and with a very gradual transition between the nerve and the sleeve.

A sleeve according to the invention for an implantable probe, capable of being wound around an elongate organ of cylindrical shape such as a nerve (VN), is shown in FIGS. 6 to 9 in order to illustrate exemplary embodiments of the invention. As illustrated in FIGS. 6 to 9 and in accordance with the invention, the sheet 26 comprises a plurality of perforations 70, located in proximity to the first and/or second transverse edge 36, 38.

The perforations 70 located in proximity to the transverse edge(s) make it possible, once the sleeve is in place around the nerve, to avoid the creation of virtual electrodes.

As a matter of fact, these perforations can on the one hand reduce the thickness of the sleeve at the ends thereof, and on the other hand reduce the difference in conductivity at the ends of the sleeve, which has the advantage of precluding unwanted generation of virtual electrodes.

Perforation is to mean, material removal so as to form a through hole or a blind hole, or an indentation (laterally open perforation opening onto the side of the transverse edge) on the sleeve in proximity to the transverse edge(s) thereof, that is—to say on the transverse edge(s) or in a zone extending up to 25% of the width of the sheet at each transverse edge, the width of the sheet being defined by the distance between the first and the second transverse edge. This material removal can be achieved in a multitude of shapes, for example round, triangular, oval, saw-tooth shaped, etc.

In addition, the perforations in proximity to the transverse edge(s) may be present over all or part of the length of the transverse edges.

Preferably, the perforations in proximity to the transverse edge(s) are made on all or part of the length of the non-beveled transverse edge(s).

Exemplary embodiments are illustrated in FIGS. 6 to 9, however, other forms of perforation can be made.

In FIGS. 6*a*, 6*b* and 6*c*, is shown a sheet 26 comprising perforations on the two transverse edges 36, 38. However, according to an alternative embodiment, not illustrated, the perforations are formed on the first or the second transverse edge 36, 38.

According to this embodiment, the perforations made on the transverse edges 36, 38 form serrated indentations on the edges. The serrations are rounded, for example in order to form one (or more) corrugated transverse edge(s) as shown in FIG. 6*b*.

The height of the corrugation is for example between 1 and 2 millimeters.

The corrugation can be made on the entire length of the transverse edge(s) or otherwise be present only on part of the length or the transverse edge(s), for example on a portion of the length of non-beveled transverse edges.

In addition, the corrugation can be made in a regular pattern or not.

Finally, the corrugation pitch can be close as shown in FIG. 6*b* or on the contrary be far apart, as shown in FIG. 6*c*.

The embodiments shown in FIGS. 6*b* and 6*c* also have the advantage of having curved shapes on the transverse edges, thereby preventing the anchoring of fibrotic tissue.

Figure 7B:
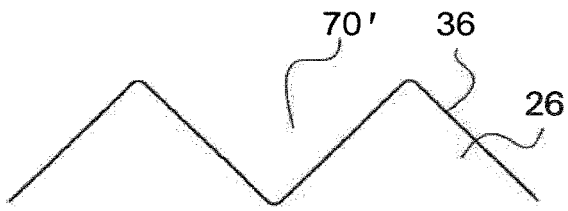
FIG. 7b is a partial view of a longitudinal edge of the sleeve according to this embodiment.

In FIGS. 7*a* and 7*b*, is shown a sheet 26 with perforations 70' on transverse edges 36, 38 so as to form indexing patterns on the saw-tooth shaped, non-rounded transverse edges. In other words, the saw-toothed edges shown in FIG. 7*b* are triangular in shape. In order to reduce the development of fibrotic tissue, tooth tips form an obtuse angle.

According to an exemplary embodiment, the distance between two tooth tips is between 2 and 4 millimeters. In addition, the height of each tooth ranges for example between 1 and 2 millimeters.

According to a particular embodiment, the teeth formed on the transverse edges all have the same height. However, according to an alternative embodiment, the teeth formed on the transverse edges are of different heights.

In addition, according to a first alternative embodiment of the serrated transverse edges, the teeth are joined to one another contiguously.

According to a second alternative embodiment of the serrated transverse edges, the teeth are spaced apart as shown in FIG. 6*c*.

According to a particular embodiment, the serrated transverse edges may be formed, alternately or not, of rounded teeth and triangular-shaped teeth.

Figure 8A:
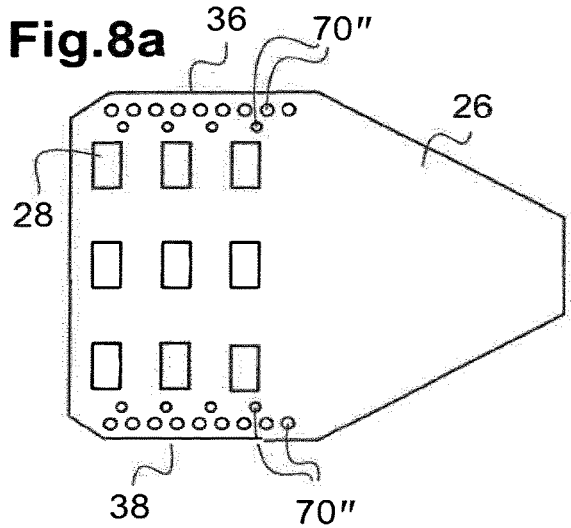
FIG. 8a is a plan view of a third embodiment of the sleeve according to the invention, in the unrolled configuration
Figure 8B:
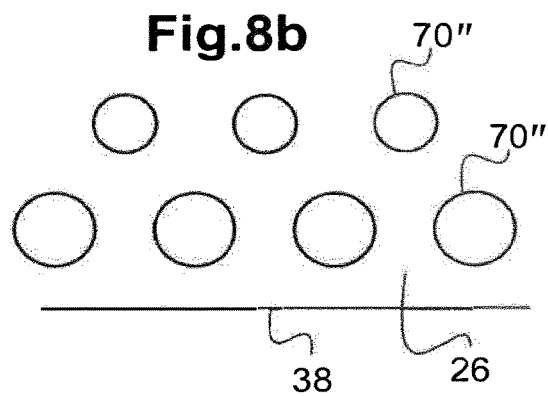
FIG. 8b is a partial view of a longitudinal edge of the sleeve according to this embodiment.
Figure 9A:
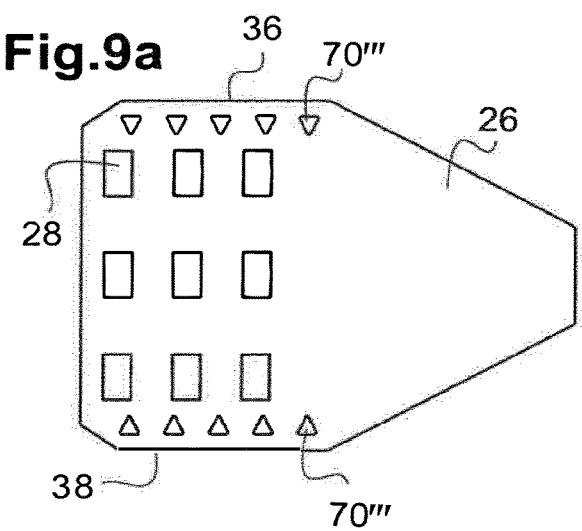
FIG. 9a is a plan view of a fourth embodiment of the sleeve according to the invention, in the unrolled configuration
Figure 9B:
FIG. 9b is a partial view of a longitudinal edge of the sleeve according to this embodiment.

According to another embodiment shown in FIGS. 8 and 9, the perforations are located in at least one zone extending up to 25% of the width of the sheet at one or more transverse edges 36, 38, the width of the sheet being defined by the distance between the first and the second transverse edge. These perforations may extend over all or part of the length of one or more transverse edges, in particular all or part of the length of one or more non-beveled transverse edges. According to this embodiment, the perforations are made in one or more zones adjacent to the transverse edges thereby reducing the thickness of the sleeve at sleeve ends when in wound condition. Thus, according to the invention, the difference in conductivity at sleeve ends is reduced. Therefore, the unwanted generation of virtual electrodes is suppressed.

In particular, FIG. 8a shows perforations 70" that are made in proximity to the two non-beveled transverse edges 36 and 38. Obviously, perforations may be made on only one transverse edge 36 or 38.

According to the embodiment shown in FIG. 8a, the perforations 70" are substantially round in shape, these perforations may be in the form of through holes or blind holes, for example, made on a single elastomer sheet 26a or 26b. These perforations may also be, for example, of substantially oblong shape. Due to the non-angular shape of these forms of perforation, there cannot be any anchoring of fibrotic tissue.

The substantially round or oblong perforations, as shown in FIG. 8b, are located in proximity to a transverse edge, in particular the non-beveled transverse edge, in one or more rows, for example in two rows. According to an exemplary embodiment, the substantially round-shaped perforations are positioned in staggered rows.

According to an exemplary embodiment, the perforations are between 10 micrometers and 500 micrometers in diameter.

FIG. 8b shows two rows of perforations 70", in which the diameter of the perforations of the first row, which is closer to the transverse edge, is different from, in particular greater than, the diameter of the perforations in the second row. Alternatively, the diameter of the perforations of the first row, in proximity to the transverse edge, may be smaller than the diameter of the perforations in the second row. According to a preferred embodiment, it is advantageous to have a gradient of perforations in the direction of the transverse edge(s).

In FIG. 9a, is shown another embodiment, in which the perforations 70''' are triangular in shape, located in at least a region extending up to 25% of the width of the sheet at one or more transverse edges 36, 38, the width of the sheet being defined by the distance between the first and the second transverse edge. The triangles, according to a particular embodiment, have rounded corners so as to prevent anchoring of fibrotic tissues. The triangle sides have for example a length between 200 micrometers and 1 millimeter.

FIG. 9a illustrates the presence of a row of triangular-shaped perforations 70''' on either side of the transverse edges. However, several rows of triangular-shaped perforations 70''' can be provided for. Similarly, triangular perforations 70''' of several dimensions can also be implemented.

Of course, the embodiments shown in FIGS. 6a to 9a can be combined.

The invention claimed is:

1. An implantable probe comprising:
a sleeve capable of being wound around an elongate organ of cylindrical shape, the sleeve comprising:
a sheet of elastically deformable material supporting at least one detection/stimulation electrode on a first face of the sheet, the sheet being prestressed to allow it to self-wind from an initial position, in which the sheet is kept stressed in the deployed state, to a final position, in which the sheet is wound freely in a spiral to form the sleeve around the organ, with the first face, which supports the electrodes, being directed towards the inside,
the sheet being delimited by an outer lateral edge of the sleeve after winding, an inner lateral edge of the sleeve after winding, and a first transverse edge joining first homologous ends of the outer lateral edge and of the inner lateral edge, and a second transverse edge joining second homologous ends of the outer lateral edge and of the inner lateral edge,
wherein the sheet comprises a plurality of perforations located along the first and/or second transverse edge, and
wherein when in the final position, the plurality of perforations reduce a difference in conductivity between the outer lateral edge and the inner lateral edge.

2. The implantable probe of claim 1, wherein the perforations are triangular in shape.

3. The implantable probe of to claim 2, wherein the triangles have rounded corners.

4. The implantable probe of claim 1, wherein the perforations are substantially round in shape.

5. The implantable probe of claim 1, wherein the perforations are located in at least one zone extending up to 25% of the width of the sheet in proximity to the first and/or second transverse edge, the width of the sheet being defined by the distance between the first and the second transverse edge.

6. The implantable probe of claim 1, wherein the perforations are formed on the first and/or second transverse edge and form a saw-tooth shape along the first and/or second transverse edge.

7. The implantable probe of claim 1, wherein the outer lateral edge is, at both ends, connected to the two transverse edges via a respective bevel edge forming an oblique angle with respect to the direction of the largest dimension of the sheet.

8. The implantable probe of claim 7, wherein the bevel edge extends over 15 to 60% of the extent of the sheet in the direction of its largest dimension.

9. The implantable probe of claim 7, wherein the perforations are located along a non-beveled portion of the first and/or the second transverse edge.

10. The implantable probe of claim 7, wherein each beveled edge forms, relative to the direction of greatest dimension of the sheet, an angle between 20 and 45°.

11. The implantable probe of claim 1, wherein the inner lateral edge is connected to the first transverse edge and the second transverse edge by a third and a fourth respective bevel edge forming a second oblique angle relative to the direction of greatest dimension of the sheet.

12. The implantable probe of claim 11, wherein the third and fourth beveled edges each form, relative to the direction of greatest dimension of the sheet, an angle between 30 and 60°.

13. A sleeve for stimulation of the vagus nerve, the sleeve comprising:
a sheet of elastically deformable material having a spiral bias so as to allow self-winding of the sheet when unstressed;
at least one detection/stimulation electrode supported by a first face of the sheet;
wherein after winding the sheet comprises an outer lateral edge, an inner lateral edge, and a first transverse edge joining first homologous ends of the outer-lateral edge and of the inner lateral edge, and a second-transverse edge joining second homologous ends of the outer lateral edge and of the inner lateral edge,
wherein the sheet comprises a plurality of perforations located along the first and/or second transverse edge; and wherein after winding, the plurality of perforations reduce a difference in conductivity between the outer lateral edge and the inner lateral edge.

14. The sleeve of claim 13, wherein the perforations are triangular in shape.

15. The sleeve of claim 14, wherein the triangles have rounded corners.

16. The sleeve of claim 13, wherein the perforations are substantially round in shape.

17. The sleeve of claim 13, wherein the perforations are located in at least one zone extending up to 25% of the width of the sheet in proximity to the first and/or second transverse edge, the width of the sheet being defined by the distance between the first and the second transverse edge.

18. The sleeve of claim 13, wherein the perforations are formed on the first and/or second transverse edge and form a saw-tooth shape along the first and/or second transverse edge.

19. The sleeve of claim 13, wherein the outer lateral edge is, at both ends, connected to the two transverse edges via a respective bevel edge forming an oblique angle with respect to the direction of the largest dimension of the sheet.

20. The sleeve of claim 13, wherein the bevel edge extends over 15 to 60% of the extent of the sheet in the direction of its largest dimension.

* * * * *